(12) United States Patent
Geslot

(10) Patent No.: US 9,550,003 B2
(45) Date of Patent: Jan. 24, 2017

(54) INSTALLATION FOR PROCESSING ARTICLES BY ELECTRON BOMBARDMENT

(71) Applicant: Serac group, La Ferte Bernard (FR)

(72) Inventor: Nicolas Geslot, Saint Christophe en Champagne (FR)

(73) Assignee: SERAC GROUP, La Ferte Bernard (FR)

( * ) Notice: Subject to any disclaimer, the term of this patent is extended or adjusted under 35 U.S.C. 154(b) by 0 days.

(21) Appl. No.: 14/293,575

(22) Filed: Jun. 2, 2014

(65) Prior Publication Data

US 2015/0034839 A1 Feb. 5, 2015

(30) Foreign Application Priority Data

Jun. 3, 2013 (FR) ...................................... 13 55040

(51) Int. Cl.
*A61L 2/08* (2006.01)
*G21K 5/02* (2006.01)
*G21K 5/08* (2006.01)
*B65B 43/46* (2006.01)
*B65B 55/08* (2006.01)
*B65B 55/16* (2006.01)

(52) U.S. Cl.
CPC ................ *A61L 2/082* (2013.01); *A61L 2/087* (2013.01); *B65B 43/46* (2013.01); *B65B 55/08* (2013.01); *B65B 55/16* (2013.01); *G21K 5/02* (2013.01); *G21K 5/08* (2013.01); *A61L 2202/121* (2013.01); *A61L 2202/23* (2013.01)

(58) Field of Classification Search
USPC . 250/453.11, 454.11, 455.11, 492.3; 422/20, 21, 22, 23
See application file for complete search history.

(56) References Cited

U.S. PATENT DOCUMENTS

| 6,529,577 | B1 | 3/2003 | Allen et al. | |
|---|---|---|---|---|
| 2011/0012030 | A1 | 1/2011 | Bufano et al. | |
| 2011/0062347 | A1* | 3/2011 | Eguchi | A61L 2/087 250/455.11 |
| 2014/0231673 | A1* | 8/2014 | Yokobayashi | B65B 55/08 250/455.11 |

FOREIGN PATENT DOCUMENTS

| EP | 2371397 | 10/2011 |
|---|---|---|
| WO | WO2013058205 | 4/2013 |
| WO | WO2013068251 | 5/2013 |

* cited by examiner

*Primary Examiner* — Nicole Ippolito
(74) *Attorney, Agent, or Firm* — Muncy, Geissler, Olds & Lowe, P.C.

(57) ABSTRACT

An installation for treating articles by radiation, the installation comprising a structure (1) having an article transport device (10) mounted thereon with a portion housed in a shielded enclosure (2) in the vicinity of at least one radiation emitter (3), the enclosure including a tunnel (40) having internal transverse partitions (51, 52, 53, 54) defining a baffle passage (50) through which there extends a segment of the transport device. The partitions are arranged in such a manner that the baffle passage extends in a plane that is substantially vertical.
A packaging installation including such a processing installation.

6 Claims, 1 Drawing Sheet

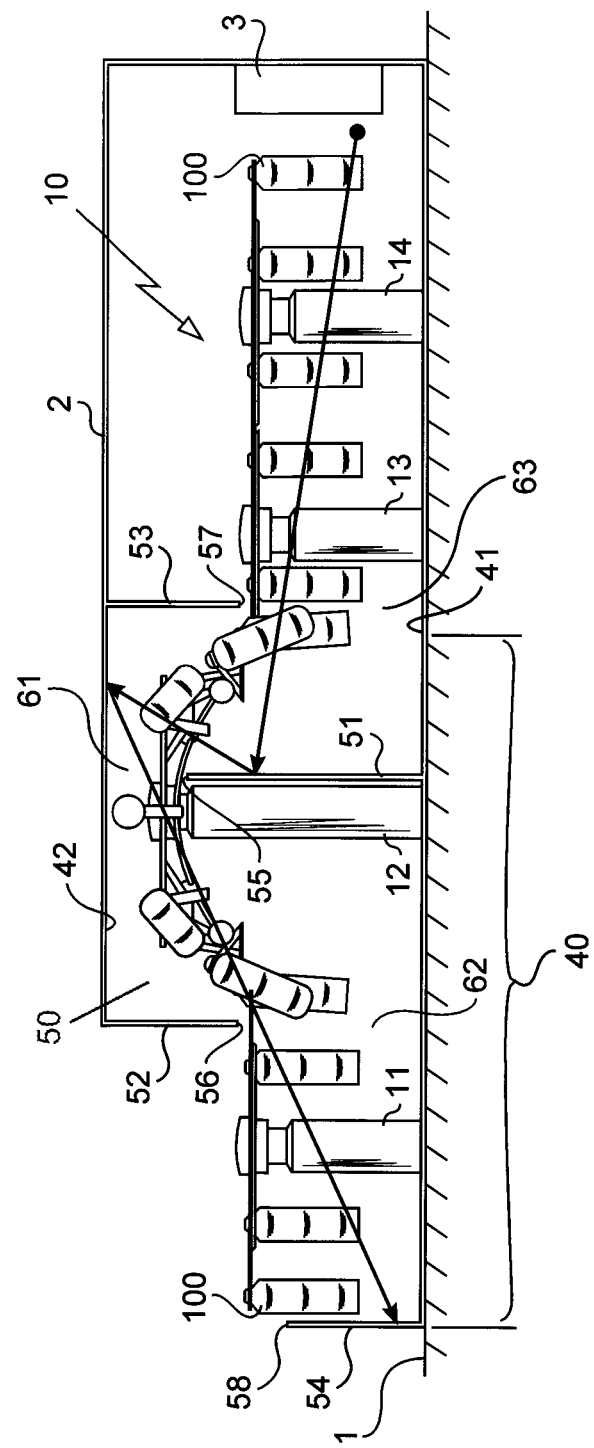

US 9,550,003 B2

INSTALLATION FOR PROCESSING ARTICLES BY ELECTRON BOMBARDMENT

BACKGROUND OF THE INVENTION

Field of the Invention

The present invention relates to an installation for processing articles by radiation and more particularly by electron bombardment.

Brief Discussion of the Related Art

It is known to sterilize containers by subjecting them to electron bombardment. Such electron bombardment is performed in a shielded enclosure seeking to confine X-rays in a zone from which operators are excluded.

To this end, an installation for treating containers by electron bombardment comprises a structure having a container transport device mounted thereon with a portion of the device housed in a shielded enclosure in the vicinity of one or more radiation emitters. The enclosure has an inlet and an outlet forming a passage for the transport device.

In order to attenuate the energy of X-rays emitted by the emitter and prevent them from escaping from the shielded enclosure, it is known to arrange shielded internal partitions in the enclosure that are arranged as a horizontal baffle between the inlet and the outlet of the shielded enclosure. The term "baffle" is used to mean that the internal partitions are arranged so as to prevent X-rays having a direct path from the emitter to the inlet or to the outlet. Thus, the X-rays produced in the environment of the emitter are reflected against the walls of the shielded enclosure and of the shielded internal partitions a number of times that is sufficient to cause them to lose substantially all of their energy before they reach the inlet or the outlet of the shielded enclosure.

Installing internal partitions makes it necessary to use intermediate container-transfer devices to enable the containers to travel past the baffles.

Although operators are very well protected by such installations, the presence of the baffles is very constraining. The installation presents the drawback of occupying a large floor area or "footprint" in particular because of the presence of the intermediate transfer devices that are of dimensions that have a direct influence on the footprint of the installation.

SUMMARY OF THE INVENTION

An object of the invention is to provide means for protecting operators acting in the vicinity of the installation for treating articles by radiation while limiting the size of the installation.

To this end, the invention provides an installation for treating articles by radiation, the installation comprising a structure having an article transport device mounted thereon with a portion housed in a shielded enclosure in the vicinity of at least one radiation emitter. The enclosure includes at least one tunnel that defines a baffle passage through which there extends a segment of the transport device, and the baffle passage extends in a plane that is substantially vertical.

Thus, arranging the baffle vertically makes it possible to ensure that the enclosure is radiation-proof while limiting the footprint of the installation. It should be observed that the articles enter and leave the enclosure by being conveyed by the transport device. When applied to containers, this makes it easier to install the treatment station in a packaging installation while enabling it to operate at a relatively high rate of throughput (as contrasted to a treatment installation from which the containers are removed in bulk, which makes it easier to arrange shielding but limits production throughput when installed in a packaging installation).

Preferably, the baffle passage is defined by walls extending transversely, projecting into the tunnel in order to define successive openings that are mutually offset heightwise.

By way of example, this produces a top opening between two bottom openings, or vice versa. This kind of embodiment makes it easier to install the transport device in the tunnel while limiting the length of the tunnel.

The invention also provides a packaging installation for packaging a substance in containers, the packaging installation including such a treatment installation connected to an upstream station and to a downstream station by segments of the transport device extending in said at least one tunnel.

The upstream station may for example be a station for cleaning the containers and the downstream station may for example be a station for filling the containers.

Other characteristics and advantages of the invention appear on reading the following description of particular, non-limiting embodiments of the invention.

BRIEF DESCRIPTION OF THE DRAWINGS

Reference is made to the sole accompanying FIGURE which is a diagram showing a portion of an installation in accordance with the invention.

DETAILED DISCUSSION OF THE PREFERRED EMBODIMENTS

With reference to the FIGURE, the treatment installation in accordance with the invention in this example is arranged for sterilizing containers by subjecting them to electron bombardment.

The installation of the invention is for taking its place in a production line, e.g. downstream from a station for blowing bottle containers and upstream from a station for filling said containers.

The installation comprises a structure 1 having mounted thereon a device for transporting containers 100 given overall reference 10.

A portion of the transport device 1 is received in a shielded enclosure 2 in the vicinity of a radiation emitter 3 contained inside the enclosure 2. The radiation emitter 3 in this example performs electron bombardment.

The enclosure has an access tunnel 40 with shielded internal partitions that extend across the tunnel 40 in order to define a baffle passage given overall reference 50 through which there extends a segment of the transport device 10.

More precisely, a first partition 51 extends from a bottom surface 41 of the tunnel 40 towards a top surface 42 of the tunnel 40 between a second partition 52 and a third partition 53, both of which extend from the top surface 42 towards the bottom surface 41. The partitions 51, 52, and 53 are substantially parallel to one another. The first partition 51 has a top edge 55 that co-operates with the top surface 42 to define a first opening 61. The second partition 52 and the third partition 53 have respective bottom edges 56 and 57 that co-operate with the bottom surface 41 to define respective second and third openings 62 and 63. The top edge 55 of the first partition 51 extends above the bottom edges 56, 57 of the second and third partitions 52 and 53. The partitions 51, 52, and 53 are spaced apart from one another and they are thus arranged to prevent X-rays passing directly from the radiation emitter 3 to the outside of the enclosure 2. As a result, the partitions 51, 52, and 53 are arranged so that the baffle passage 50 extends in a plane that is substantially vertical (the plane of the FIGURE in the drawings).

In this example, the tunnel has a fourth shielded partition 54 extending across the tunnel 40 at its end that is situated the furthest out from the enclosure 2. The fourth partition 54 extends from the bottom surface 41 and its top edge 58 extends below the bottom edge 56 of the second partition 52. The fourth partition 54 reinforces the radiation-proofing of the enclosure and co-operates with the second partition 52 to define an inlet/outlet opening of the tunnel 40.

The term "shielded" is used to mean that the wall or partition is proof against electrons and X-rays. The shielded wall or partition thus has a layer of lead covered in a sheet of stainless steel.

In this example, the transport device 10 has conventional transport stars 11, 12, 13, and 14 rotatably mounted on the structure 1 and they are connected to a device (not shown) for driving them in rotation. The transport stars 11, 12, 13, and 14 are tangential to one another, and each of them is provided with means for gripping containers, such as clamps for gripping containers by the neck.

The transport star 11 is situated between the fourth partition 54 and the second partition 52. It contributes to introducing containers 100 into the tunnel 40 or to evacuating the containers 100 from the tunnel 40. The transport star 11 is tangential to at least one container transport device (not shown) arranged to load and unload the transport star 11.

The transport star 12 is mounted in the vicinity of the first partition 51 and is provided with means for causing the containers to be tilted over the top edge 55 of the first partition 51. The star has a platform extending over the top edge 55 and across it between the second and third partitions 52 and 53. The container-gripping clamps are mounted on the platform of the transport star 12 to pivot about respective horizontal axes between a position in which they hold the containers in a vertical position and a position in which they hold the containers in a horizontal position so as to enable the containers to be passed over the top edge 55 while in a substantially horizontal position, and so as to enable the containers to be exchanged while in the vertical position both with the transport star 11, and also with the transport star 13 that is situated in the vicinity of the third partition 53.

The transport stars 13 and 14 have their axes of rotation on the side of the third partition 53 that is remote from the second partition 52. The platform of the transport star 13 extends across and under the bottom edge 57. The transport star 13 is adjacent to the radiation emitter 3.

The platforms of the transport stars 11, 13, and 14 are at the same level. The gripper clamps of the transport star 12 are also at the same level as said platforms when said clamps are in their position for holding the containers in a vertical position.

Such stars are themselves known and are therefore not described in detail herein.

Naturally, the invention is not limited to the embodiment described but covers any variant coming within the ambit of the invention as defined by the claims.

In particular, the transport device may have transport stars, linear conveyors, or any other equipment enabling the containers to be transported.

The installation may have some other number of transport stars.

The arrangement of these partitions may be different from that shown. More precisely, the first partition could extend from the top surface 42 of the tunnel 40 towards the bottom surface 41 of the tunnel 40 between the second and third partitions, both extending from the bottom surface 41 towards the top surface 42. The first position would then have a bottom edge co-operating with the bottom surface 41 to define the first opening. The second partition and the third partition would then have respective top edges co-operating with the top surface 42 to define the second and third openings, respectively. The bottom edge of the first partition would then extend lower than the top edges of the second partition and of the third partition. The tunnel could also be defined by top and bottom walls extending in a zigzag configuration in order to define the vertical baffle passage. Nevertheless, such an arrangement would be more complex to fabricate than those described above.

The installation could include an inlet tunnel and an outlet tunnel, or it could have a single tunnel acting both as the inlet and as the outlet of the installation.

The installation could have emitters that are carried by the star 14 and/or one or more emitters that are stationary, or it could have only one or more stationary emitters, or it could have only emitters that are on carried by the star 14.

The stars could have a structure different from that described, in particular concerning how they grip the containers.

The invention may be applied to articles other than containers and/or to other types of radiation.

The invention claimed is:

1. An installation for treating articles by radiation, the installation comprising a structure (1) having an article transport device (10) mounted thereon with a portion housed in a shielded enclosure (2) in the vicinity of at least one radiation emitter (3), wherein the enclosure has at least one tunnel (40) defining a baffle passage (50), along which there extends a segment of the transport device arranged for supporting the articles through the baffle passage, and the baffle passage extends in a plane that is substantially vertical, the segment of the transport device comprising a rotary star having a vertical axis of rotation, and the rotary star extending above a top edge of a first partition extending vertically from a bottom structure of the tunnel.

2. An installation according to claim 1, wherein the baffle passage is defined by walls extending transversely, projecting into the tunnel in order to define successive openings that are mutually offset heightwise.

3. An installation according to claim 2, wherein a first partition (51) extends from a bottom structure (41) of the tunnel (40) towards a top surface (42) of the tunnel between second and third partitions (52, 53) extending from the top surface towards the bottom surface, the first partition has a top edge (55) that co-operates with the top surface to define a first opening (61), the second and third partitions have bottom edges (56, 57) co-operating with the bottom surface to define respective second and third openings (62, 63), the top edge of the first partition being higher than the bottom edges of the second and third partitions.

4. An installation according to claim 3, wherein the tunnel (40) has a shielded fourth partition (54) extending transversely relative to the tunnel (40) at its end that is situated furthest out from the enclosure (2), the fourth partition (54) extending from the bottom surface (41) and having its top edge (58) extending below the bottom edge (56) of the second partition (52).

5. An installation according to claim 3, wherein the rotary star is mounted in the vicinity of the first partition and provided with means for causing the articles to tilt over the top edge of the first partition.

6. A packaging installation for packaging a substance in containers, the packaging installation including a treatment installation according to claim 1, the treatment installation being connected to an upstream station and to a downstream station by segments of the transport device extending in said at least one tunnel.

\* \* \* \* \*